United States Patent [19]

Sauer et al.

[11] Patent Number: 6,077,478

[45] Date of Patent: Jun. 20, 2000

[54] MICROWAVE POWERED STERILE ACCESS PORT

[75] Inventors: Richard L. Sauer, League City, Tex.; James E. Atwater, Eugene, Oreg.; Roger W. Dahl, Tenmile, Oreg.; Frank C. Garmon, Canyonville, Oreg.; Teddie D. Lunsford, Sutherlin, Oreg.; William F. Michalek, Roseburg, Oreg.; Richard R. Wheeler, Jr., Azalea, Oreg.

[73] Assignee: The United States of America as represented by the Administrator of the National Aeronautics and Space Administration, Washington, D.C.

[21] Appl. No.: 09/111,371

[22] Filed: Jun. 30, 1998

Related U.S. Application Data

[60] Provisional application No. 60/051,605, Jul. 2, 1997.

[51] Int. Cl.⁷ ........................................................ A61L 2/08
[52] U.S. Cl. ........................... 422/21; 219/682; 219/704; 219/710; 219/719; 219/750; 422/26; 422/38; 422/292; 422/307
[58] Field of Search ................................... 422/21, 26, 1, 422/38, 307, 292, 186; 219/678, 682, 702, 704, 710, 719, 750

[56] References Cited

U.S. PATENT DOCUMENTS

| | | |
|---|---|---|
| 3,986,508 | 10/1976 | Barrington . |
| 4,614,514 | 9/1986 | Carr et al. ................................ 604/113 |
| 5,246,674 | 9/1993 | Katschnig et al. ....................... 422/303 |
| 5,250,261 | 10/1993 | Porte ......................................... 422/63 |
| 5,321,222 | 6/1994 | Bible et al. ............................. 219/745 |
| 5,382,406 | 1/1995 | Kruger et al. ............................ 422/28 |
| 5,445,180 | 8/1995 | Divall ....................................... 137/15 |
| 5,486,478 | 1/1996 | Kuriyama .................................. 436/52 |
| 5,505,905 | 4/1996 | Corby et al. ............................ 422/102 |
| 5,721,286 | 2/1998 | Lauf et al. ................................ 522/1 |
| 5,795,552 | 8/1998 | Corby et al. ............................ 422/294 |

OTHER PUBLICATIONS

Atwater et al., "Development and Testing of the Microwave Sterilizable Access Port Prototype", SAE Technical Paper Series 961567, 26th International Conference on Enviromental Systems, Monterey, California (Jul. 8–11, 1996).

*Primary Examiner*—Krisanne Thornton
*Attorney, Agent, or Firm*—Hardie R. Barr

[57] ABSTRACT

A device and method for elimination of contamination during transfer of materials either into or from bioreactors, food containers, or other microbially vulnerable systems. Using microwave power, thermal sterilizations of mating fixtures are achieved simply, reliably, and quickly by the volatilization of small quantities of water to produce superheated steam which contacts all exposed surfaces.

19 Claims, 10 Drawing Sheets

FIG. 1

CLOSED DURING NORMAL FLOW
AND POST ACCESS STERILIZATION
FIG. 2A

CLOSED DURING STERILIZATION
FIG. 2B

OPEN DURING ACCESS
FIG. 2C

CLOSED CONFIGURATION

FIG. 3A

ACCESS CONFIGURATION

MICROWAVE POWERED STERILE ACCESS PORT

CROSS REFERENCES TO RELATED INVENTIONS

In accordance with 35 U.S.C. Section 120, applicants claim benefit of filing date of copending Provisional Patent application Ser. No. 60/051,605, filed Jul. 2, 1997.

GOVERNMENT CONTRACT

The invention described herein was made in performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

The invention relates generally to a microwave powered sterilizer and more particularly to a microwave powered sterilizer employing superheated steam.

Aseptic removal of samples and products and the addition of materials to sterile systems is frequently compromised by the lack of a reliable means of sterilizing the mating fixtures. Great care is required to prevent the contamination of microbially vulnerable systems such as samples for microbiological analysis, tissue cultures, fermentors, and mammalian cell bioreactors by microorganisms of external origin. Of equal importance is the prevention of contamination of individuals or the environment by virulent pathogens or by genetically engineered organisms of unknown pathogenicity which may be confined within an enclosure. The primary opportunities for entry or escape of microbes occur during the act of sampling, during the harvesting of products, or during the introduction of new materials, such as nutrients or inoculum, into a system. At these times, the system is exposed to the external environment. Routine aseptic practices are not always effective. Contamination of microbial specimen s as an artifact of the sample collection procedure is a common occurrence. Cultures of mammalian cells are particularly vulnerable to microbial contamination due to the complexity of nutrient media and the lengthy periods required for cell growth. Contamination of these systems is particularly costly. Development of the microwave sterilizable access port according to the present invention has resulted in a reliable means to gain access to microbially vulnerable systems in which the possibility of contamination has been eliminated.

SUMMARY OF THE INVENTION

The microwave sterilizable access port according to the present invention is a simple device for the elimination of contamination during transfer of materials either into or from bioreactors or other microbially vulnerable systems. Using microwave power, thermal sterilizations of mating fixtures are achieved simply, reliably, and very quickly by the volatilization of minute quantities of water to produce superheated steam which contacts all exposed surfaces.

Broadly, the present invention provides a method for sterile transfer of a fluid sample to or from a biological system. The method includes: (a) connecting a specimen transfer device having a penetrable septum to a sterilization chamber including a penetrating element for fluid communication with the biological system; (b) placing a quantity of water in the sterilization chamber; (c) irradiating the sterilization chamber with microwave energy to vaporize the water and superheat the resulting steam to sterilize the sterilization chamber and an exposed surface of the septum; and (d) penetrating the septum with the penetrating element to establish fluid communication between the specimen transfer device and the biological system.

The specimen transfer device preferably includes a septum holder connected to the septum, a transfer tube sealed to the septum holder and a syringe attached to the transfer tube. The method preferably includes operating a barrel in the syringe to transfer the sample between the syringe and the biological system. The biological system preferably includes a flow-through valve, and the method preferably includes moving the valve between a sterilization position wherein the sterilization chamber is sealed with respect to the flow-through valve, and an access position wherein the penetrating element is in fluid communication with the flow-through valve. The penetrating element preferably comprises a needle stub tube. The sterilization chamber preferably includes a wall made of a material having a strong dielectric loss characteristic such as silicon carbide. Preferably, a maximum duration of the irradiation is controlled by either a temperature switch connected to a thermocouple adjacent to the sterilization chamber, or a maximum fixed time set by a time delay relay. The method preferably includes the step of sealing the sterilization chamber prior to the irradiation. The position of the specimen transfer device relative to the sterilization chamber is preferably controlled by a three-position cam having an open position in which the septum is spaced from the sterilization chamber to allow the quantity of water to be placed in an open port of the sterilization chamber, a sterilization position in which the septum is received in the port to seal the sterilization chamber, and an access position in which the septum is pierced by the penetrating element. The method can also include opening a vent from the sterilization chamber after the irradiation, but before the septum penetration.

In another aspect, the present invention provides apparatus for sterile transfer of a fluid sample to or from a biological system. The apparatus includes a sterilization chamber having an inlet port. A specimen transfer device has a septum-sealed end adapted to be received in and seal the inlet port. A needle stub tube is in fluid communication between the sterilization chamber and a flow-through valve to the biological system. The valve has a closed position preventing fluid communication between the needle stub tube and the biological system, and an open position to allow fluid communication between the needle stub tube and the biological system. A microwave power supply is adapted to irradiate the sterilization chamber with microwaves. The specimen transfer device is movable with respect to the needle stub tube to pierce the septum with the needle stub tube. The sterilization chamber can have a wall made of a material having a strong dielectric loss characteristic such as silicon carbide.

The specimen transfer device preferably includes a septum holder connected to the septum, a transfer tube connected to the septum holder and a syringe connected to the transfer tube. A rotating cam can be used for positioning the specimen transfer device relative to the sterilization chamber between an open position, a sterilization position and an access position. In the open position, the septum is spaced from the inlet port so as to allow for the introduction of water into the sterilization chamber. In the sterilization position, the septum is received in the inlet port to seal the sterilization chamber, but the septum remains spaced from the needle stub tube. In the access position, the needle stub tube penetrates the septum for the transfer of the fluid sample to or from the biological system. The apparatus can also include a pressure release valve for venting the sterilization chamber after microwave irradiation, but before penetration of the septum.

The apparatus preferably includes a control circuit for operating the microwave power supply. The control circuit includes a temperature switch connect ed to a thermocouple adjacent to the sterilization chamber to turn off the microwave power supply when the sterilization chamber reaches a predetermined temperature. A time delay relay is provided to turn off the microwave power supply if the microwave power is supplied for a pre-determined period of time. A coaxial cable can be used to couple the microwave power supply to the sterilization chamber. The microwave power supply preferably includes a magnetron, a transmission antenna disposed between a fixed end-plate and a variable end-plate and pick-up antenna from the coaxial cable disposed between the end-plate. The variable end-plate is adjustable to tune the microwave power supply for maximum microwave transmission.

BRIEF DESCRIPTION OF THE DRAWINGS

FIGS. 2A–2D are cross-sectional views of an in-line valve showing different valve positions.

DESCRIPTION OF THE PREFERRED EMBODIMENTS

Figure 1:
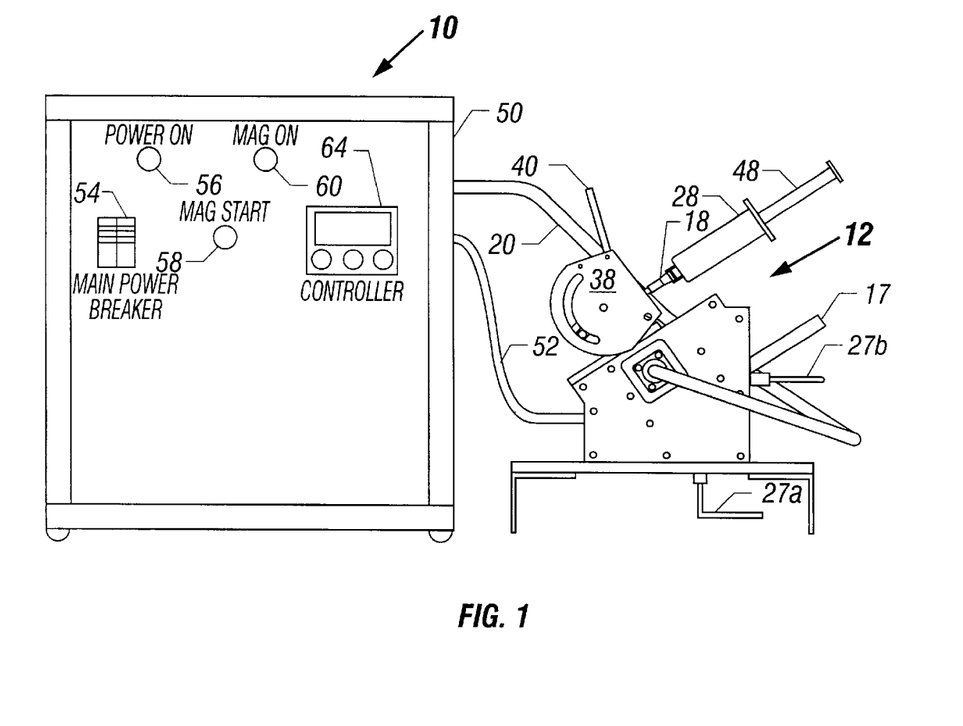
FIG. 1 is a schematic drawing of a prototype microwave sterilizable access port system according to the present invention.
Figure 2A:
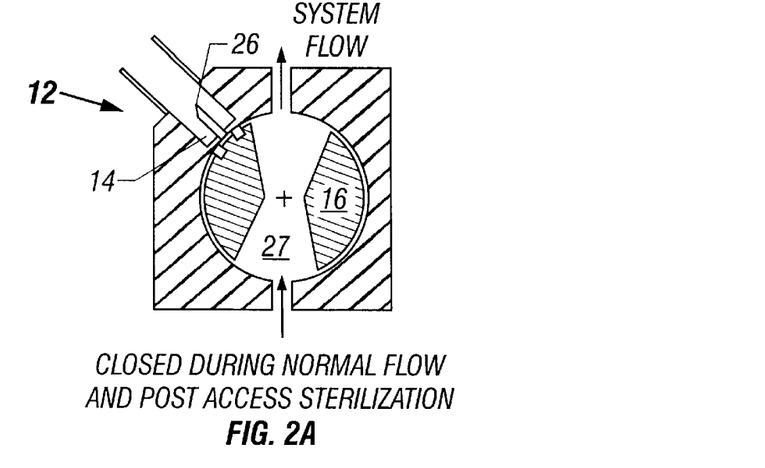
Figure 2B:
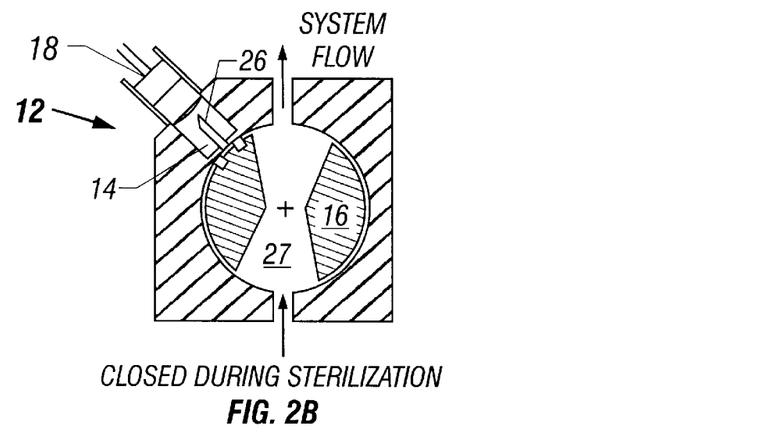
Figure 2C:
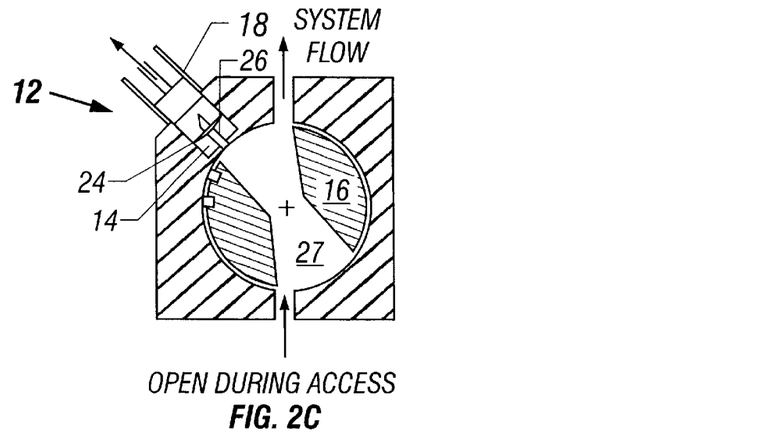
Figure 3A:
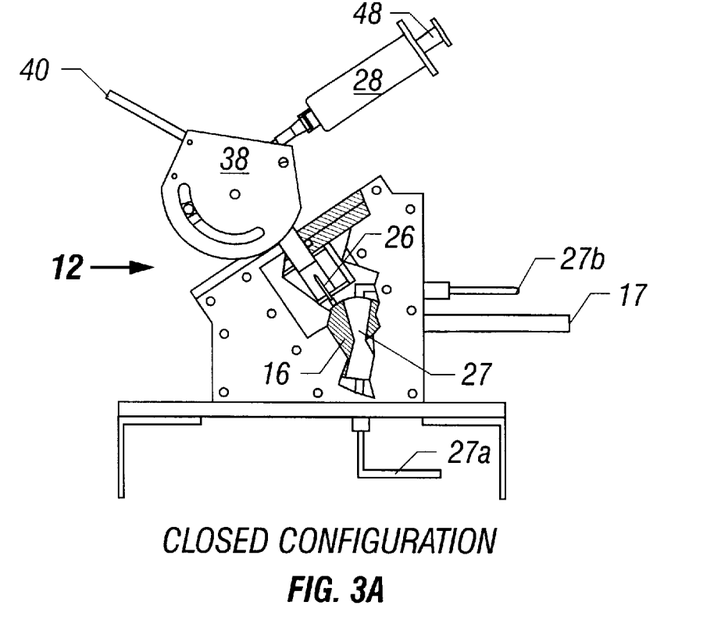
FIGS. 3A and 3B are side sectional views, partially cut away, representing closed and access configurations of the in-line valve.
Figure 3B:
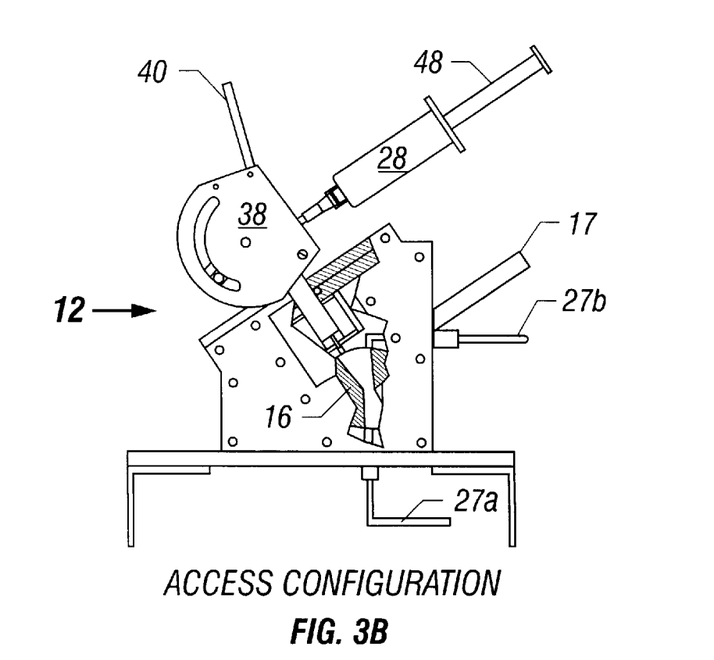
Figure 5:
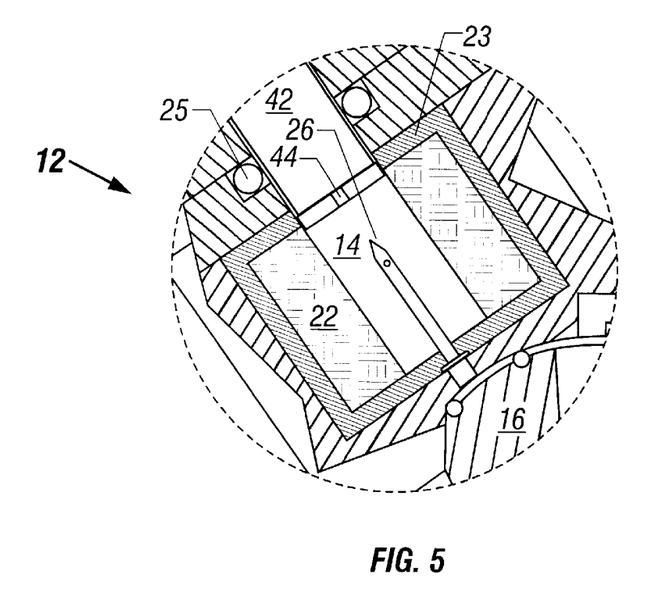
FIG. 5 is a schematic illustration of the inside of the sterilization chamber.
Figure 6A:
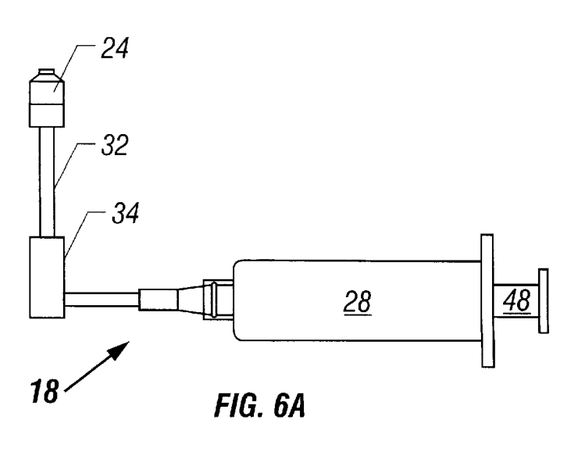
FIG. 6A is a perspective view showing the specimen transfer device.
Figure 6B:
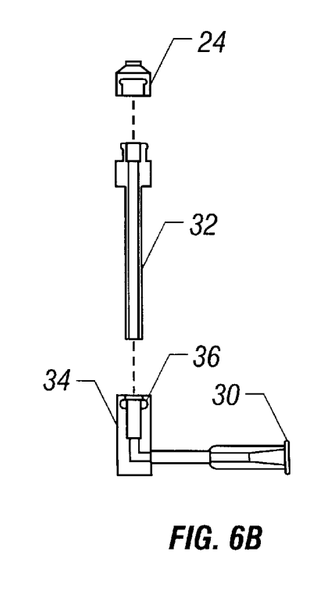
FIG. 6B is an exploded view showing the septum, septum holder and transfer tube of the specimen transfer device of FIG. 6A.
Figure 7:
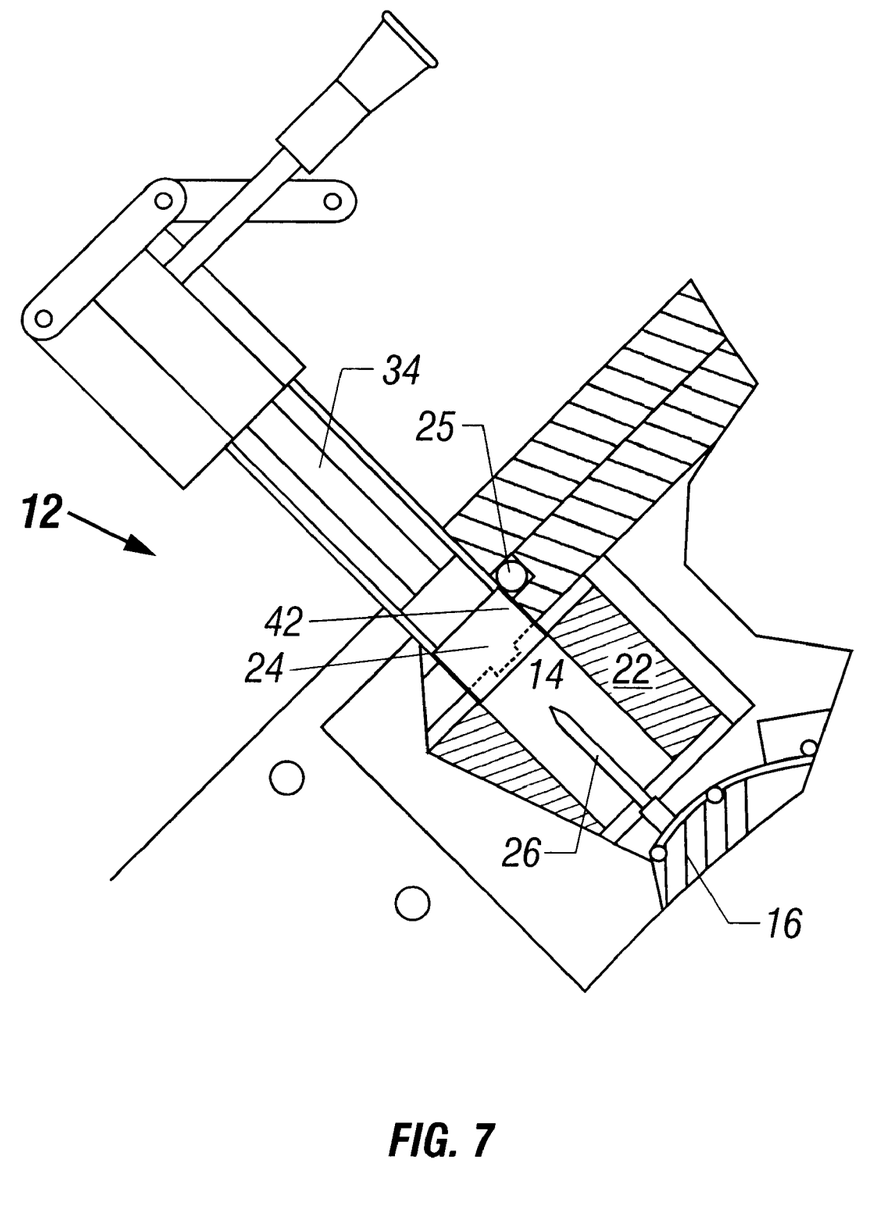
FIG. 7 is a side sectional view showing the sterile transfer device installed inside the sterilization chamber.

The microwave sterilizable access port, illustrated in FIG. 1, consists of two primary components: 1) the microwave power controller 10 and 2) the access port 12. The access port 12 includes a sterilization chamber 14 (FIGS. 5 and 7), an in-line valve plug 16 (FIGS. 2 and 3), and a specimen transfer device 18 (FIGS. 6 and 7). During normal operation the in-line valve plug 16 opened by lever or handle 17 is in the "closed" position, and the system is isolated. During specimen transfer, the pre-sterilized septum-containing specimen transfer device 18 is loaded into the sterilization chamber. Microwave energy is transferred from the microwave power controller 10 to the access port via a coaxial cable 20. Microwave energy couples directly with a silicon carbide (SiC) block 22 (FIG. 5) inside the sterilization chamber 14 and with a small amount of introduced water. The water rapidly flashes to steam which then superheats, pressurizes the chamber 14, and provides a wet thermal sterilization of all exposed surfaces. Temperature is monitored using a thermocouple (not shown) mounted in the SiC block 22 which is encapsulated in silicone/glass matt 23. When the operating temperature is achieved, microwave power is automatically discontinued. Access to the system is gained by penetrating the now sterile septum 24 face with the needle stub tube 26 and by rotating the in-line valve plug 16 to the "access" position wherein the flow-through passage 27 of the biological system is in fluid communication with the needle stub tube 26. The biological system includes inlet passage 27a and outlet passage 27b for circulation through the passage 27. Specimens are collected or introduced via a syringe 28 which mates with the specimen transfer device 18 by a Luer Lock connection 30. As seen in FIGS. 6A and 6B, the specimen transfer device 18 also includes septum holder 32 and transfer tube 34 secured at O-ring seal 36.

Figure 4A:
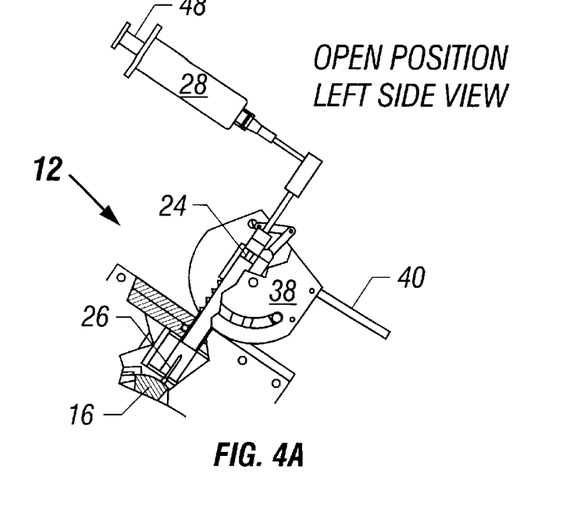
FIGS. 4A–4C are side sectional views, partially cut away, showing three positions of the access port cam.
Figure 4B:
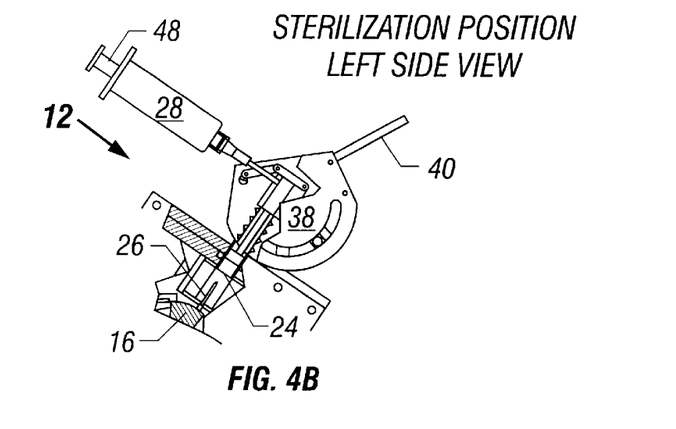
Figure 4C:
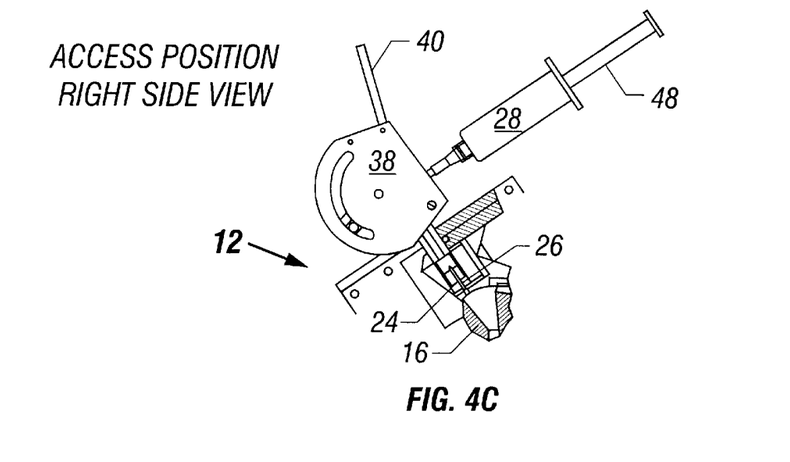
Figure 8:
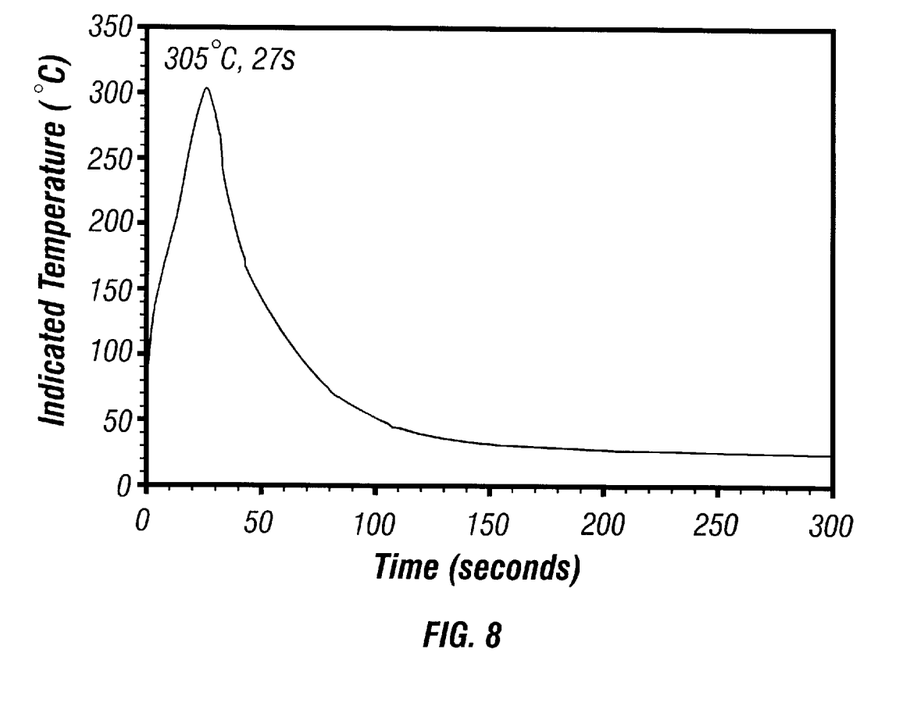
FIG. 8 is a time/temperature profile for a typical sterilization event.

Positioning of the specimen transfer device 18 within the access port 12 for installation, sterilization, and puncture of the septum 24 is controlled by a 3-position rotating cam 38 which is operated by means of lever 40. The three positions of the rotating cam 38 are illustrated in FIGS. 4A, 4B and 4C, and correspond respectively to: 1) open, 2) sterilization and 3) access positions. In the open position, approximately 500 microliters (500/$\mu$L) of water are added to the sterilization chamber 14 prior to installation of the specimen transfer device 18. The access port 12 houses a cylindrical aperture 42 into which the specimen transfer device 18 (FIGS. 6A and 6B) is inserted. At the bottom of this aperture 42 is a smaller hole 44 through which access is gained to the sterilization chamber 14 (FIG. 5). Distilled water is introduced through the small hole 44 with care not to deposit water within the larger cylindrical aperture 42. The pre-sterilized specimen transfer device 18 is then inserted into the aperture 42, septum 24 first (FIG. 7). By rotating the 3-position cam 38 to the "sterilization" position, the septum 24 seal is established by means of O-ring seal 25 and the sterilization chamber 14 is closed to the outside environment. Electrical power is applied to the magnetron 46 (FIGS. 9 and 11) and microwave power rapidly heats the SiC block 22. The 500 $\mu$L of water quickly vaporizes, exposing all surfaces in the sterilization chamber 14 to superheated steam. After a few seconds, the temperature begins to rise rapidly. When the temperature reaches approximately 300° C. (572° F.), the power to the magnetron 46 is automatically terminated and a solenoid vent valve (not shown) opens, releasing a small amount of steam and condensate. The microwave power cycle lasts for approximately 30 seconds. A typical temperature profile for the sterilization event is shown in FIG. 8.

The 3-position cam 38 is then rotated into the "access" position. As the mechanism rotates, the sterilized septum 24 surface is pierced by the sterile needle stub tube 26. A specimen can now be either introduced or collected by shifting the in-line valve plug 16 on the access port assembly to the "access" position (FIGS. 2C, 3B and 4C) and by manipulating the syringe barrel 48 appropriately. To terminate access to the system, the in-line valve plug 16 is closed, the three-position cam 38 is moved back to the "open" position, and the specimen transfer device 18 is removed.

Figure 9:
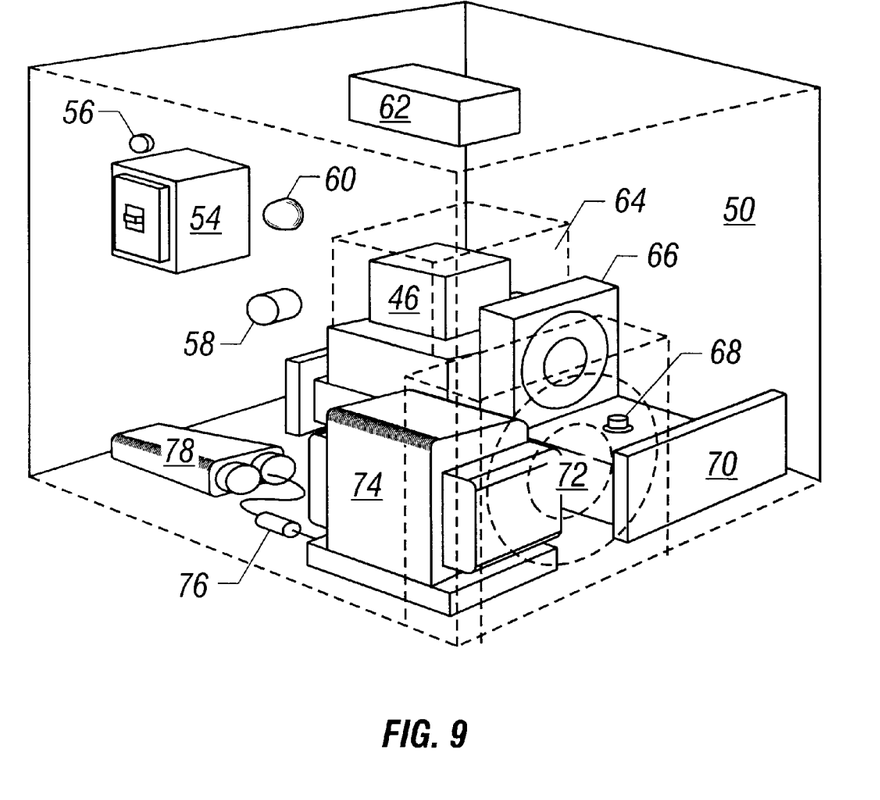
FIG. 9 is an illustration of the physical layout of a prototype microwave power controller according to one embodiment of the present invention.
Figure 10:
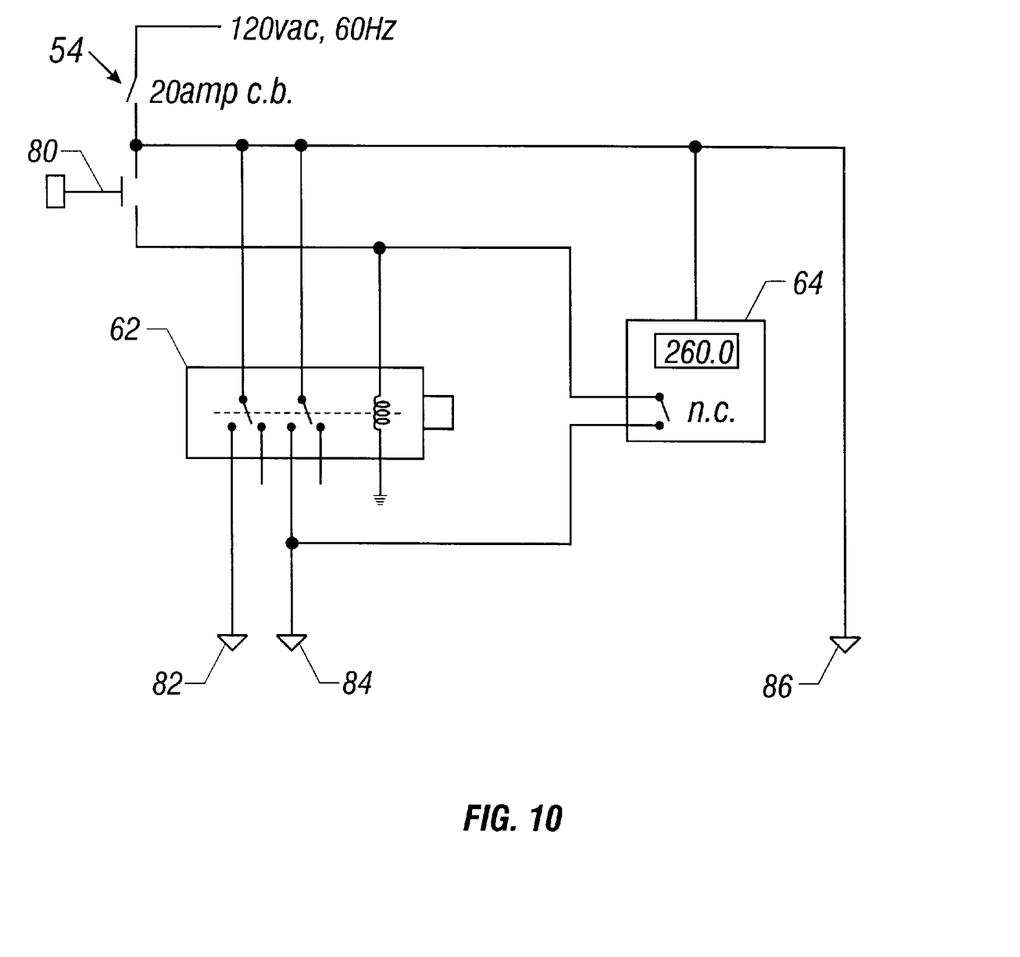
FIG. 10 is a schematic diagram of the electrical control for the microwave sterilizable access port system.
Figure 11:
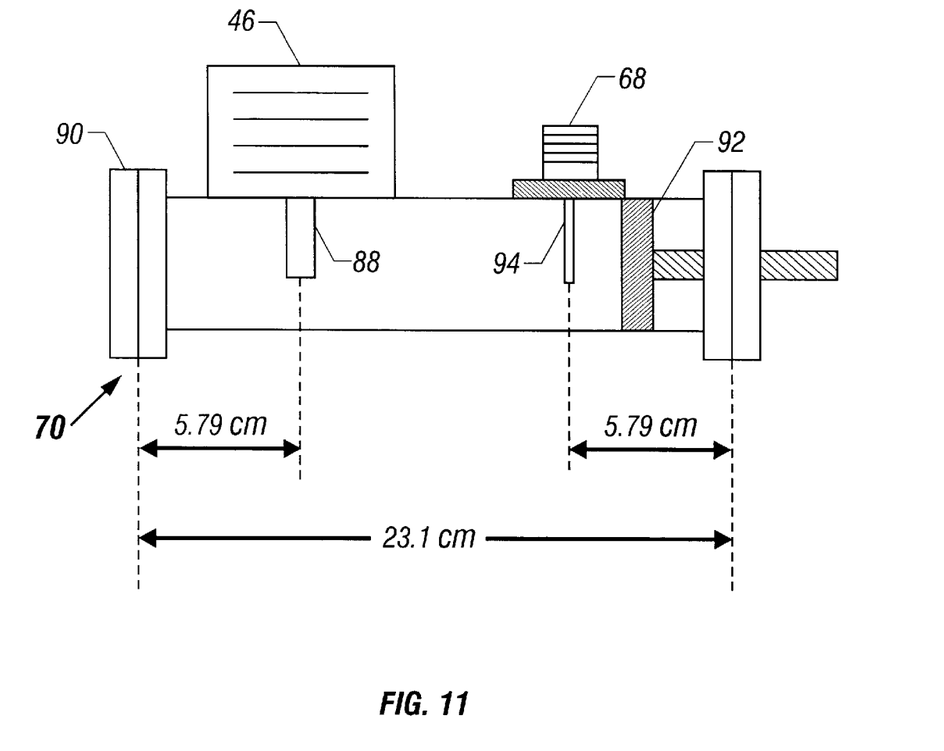
FIG. 11 is a schematic diagram of the microwave launcher construction for the microwave sterilizable access port system.

The microwave power controller (MPC) cabinet 50 houses the microwave power generation hardware and control electronics. The coaxial cable 20 provides microwave power transmission from the MPC to the access port 12 and the controller cable 52 transmits other electrical signals between the MPC and the access port 12. Sterilization events are initiated and monitored at the MPC. A block diagram identifying the components for the MPC is shown in FIG. 9, and shows exemplary positioning of the main power circuit breaker 54, power on light 56, magnetron on button 58, magnetron on light 60, time delay relay 62, temperature controller 64, magnetron fan 66, SC female coaxial connection 68, microwave launcher 70, equipment cooling fan 72, transformer 74, diode 76 and capacitor 78. The wiring diagram for the MPC control system shown in FIG. 10 illustrates circuit breaker 54, momentary sterilize switch 80, time delay relay 62, temperature controller 64 (which can be an Omega CN 76133-pv, for example), steam purge solenoid (normally open, not shown) power supply 82, magnetron power supply 84 and fan power supply 86. Time delay relay 62 is used to provide a fixed time safety limit for the microwave Sterilizable Access Port. The time delay relay 62, set for approximately 45 seconds, is "latched on" through the temperature controller's normally closed (n.c.) control contacts, allowing sterilization to continue. Sterilization proceeds until the time delay relay 62 is de-energized. This happens when either the temperature setpoint for the controller 64 is reached thereby opening the controller's normally closed (n.c.) contacts, or the upper time limit, set by the time delay relay 62 is exceeded. The microwave launcher 70, constructed of WR 284 waveguide, shown in FIG. 11 illustrates magnetron 46, transmission antenna 88, fixed end-plate 90, variable end-plate 92, pick-up antenna 94 and coaxial connection 68. Variable end-plate 92 allows tuning of the power transmission efficiency from the waveguide section to the coaxial transmission line.

The unique properties of microwaves, which couple directly with materials having strong dielectric loss characteristics such as water and silicon carbide to produce heat, have been exploited to produce the rapid, localized, and effective sterilization methodology embodied in the design and operation of the prototype microwave sterilizable access port according to the present invention. The use of silicon carbide as a microwave absorbing medium has resulted in an extremely rapid sterilization chamber heat-up, producing maximum temperatures greater than or equal to 300'C in approximately 30 seconds.

The introduction of small quantities of water (approximately 500/$\mu$L) which flashes to steam during sterilization provides a thermally active vapor which contacts all exposed mating surfaces, and which completely destroys any viable microorganisms or spores which may be present. Wet thermal sterilizations of systems contaminated with a variety of bacteria, yeasts, and molds have been achieved with the apparatus and method of the present invention.

The utility of the novel hardware has been demonstrated by numerous repetitive transfers of sterile media through a sterilization chamber which has been intentionally contaminated with approximately 1 million CFU of *Bacillus stearothermophilus*, the thermophillic spore forming bacterium which is used as the standard microbial challenge for wet heat and steam sterilization methodologies. Bi-directional transfer of sterile media has been demonstrated. Tables I and II present the results of extensive microbial challenges of the specimen withdrawal and specimen introduction procedures, respectively. No microbial survivors were recovered in any of the 80 replicate experiments.

TABLE I

| Test | Initial CFU | Septum CFU | Specimen CFU | Media CFU | Time to Max. Temperature(s) | Max. T (° C.) |
|---|---|---|---|---|---|---|
| Prototype Specimen Withdrawal Test - 305° C., 500 $\mu$L H$_2$O - *B. stearothermophilus*. | | | | | | |
| 1 | $4.2 \times 10^6$ | – | – | – | 35 | 303 |
| 2 | $4.2 \times 10^6$ | – | – | – | 36 | 304 |
| 3 | $4.2 \times 10^6$ | – | – | – | 34 | 305 |
| 4 | $4.2 \times 10^6$ | – | – | – | 36 | 305 |
| 5 | $4.2 \times 10^6$ | – | – | – | 35 | 304 |
| 6 | $4.2 \times 10^6$ | – | – | – | 35 | 305 |
| 7 | $4.2 \times 10^6$ | – | – | – | 33 | 304 |
| 8 | $4.2 \times 10^6$ | – | – | – | 33 | 304 |
| 9 | $4.2 \times 10^6$ | – | – | – | 34 | 304 |
| 10 | $4.2 \times 10^6$ | – | – | – | 33 | 305 |
| 11 | $4.2 \times 10^6$ | – | – | – | 32 | 305 |
| 12 | $4.2 \times 10^6$ | – | – | – | — | 305 |
| 13 | $7.5 \times 10^6$ | – | – | – | 32 | 305 |
| 14 | $7.5 \times 10^6$ | – | – | – | 32 | 305 |
| 15 | $7.5 \times 10^6$ | – | – | – | 30 | 305 |
| 16 | $7.5 \times 10^6$ | – | – | – | 32 | 305 |
| 17 | $7.5 \times 10^6$ | – | – | – | 30 | 307 |
| 18 | $7.5 \times 10^6$ | – | – | – | 32 | 305 |
| 19 | $7.5 \times 10^6$ | – | – | – | 36 | 305 |
| 20 | $7.5 \times 10^6$ | – | – | – | 33 | 304 |
| 21 | $7.5 \times 10^6$ | – | – | – | 33 | 305 |
| 22 | $7.5 \times 10^6$ | – | – | – | 30 | 305 |
| 23 | $7.5 \times 10^6$ | – | – | – | 31 | 306 |
| 24 | $7.5 \times 10^6$ | – | – | – | 29 | 304 |
| Prototype Specimen Withdrawal Test - 305° C., 500 $\mu$L H$_2$O. | | | | | | |
| 25 | $3.4 \times 10^5$ | – | – | – | 31 | 306 |
| 26 | $3.4 \times 10^5$ | – | – | – | 31 | 305 |
| 27 | $3.4 \times 10^5$ | – | – | – | 31 | 305 |
| 28 | $3.4 \times 10^5$ | – | – | – | 30 | 306 |
| 29 | $3.4 \times 10^5$ | – | – | – | 37 | 304 |
| 30 | $3.4 \times 10^5$ | – | – | – | 28 | 306 |
| 31 | $3.4 \times 10^5$ | – | – | – | 33 | 304 |
| 32 | $3.4 \times 10^5$ | – | – | – | 30 | 306 |
| 33 | $3.4 \times 10^5$ | – | – | – | 33 | 392 |
| 34 | $3.4 \times 10^5$ | – | – | – | 28 | 305 |
| 35 | $3.4 \times 10^5$ | – | – | – | 29 | 305 |
| 36 | $3.4 \times 10^5$ | – | – | – | 32 | 305 |
| 37 | $1.6 \times 10^5$ | – | – | – | 31 | 306 |
| 38 | $1.6 \times 10^5$ | – | – | – | 31 | 304 |
| 39 | $1.6 \times 10^5$ | – | – | – | 28 | 305 |
| 40 | $1.6 \times 10^5$ | – | – | – | 29 | 305 |
| 41 | $1.6 \times 10^5$ | – | – | – | 33 | 305 |
| 42 | $1.6 \times 10^5$ | – | – | – | 30 | 305 |
| 43 | $1.6 \times 10^5$ | – | – | – | 33 | 307 |
| 44 | $1.6 \times 10^5$ | – | – | – | 30 | 306 |
| 45 | $1.6 \times 10^5$ | – | – | – | 30 | 307 |
| 46 | $1.6 \times 10^5$ | – | – | – | 27 | 307 |
| 47 | $8.1 \times 10^5$ | – | – | – | 27 | 307 |
| 48 | $8.1 \times 10^5$ | – | – | – | 28 | 306 |

+ = Survivors Present
– = No Survivors Present

TABLE II

| Test | Initial CFU | Septum CFU | Specimen CFU | Media CFU | Time to Max. Temperature(s) | Max. T (° C.) |
|---|---|---|---|---|---|---|
| Prototype Specimen Introduction Test - 305° C., 500 $\mu$L H$_2$O - *B. stearothermophilus*. | | | | | | |
| 1 | $8.1 \times 10^5$ | – | – | – | 28 | 306 |
| 2 | $8.1 \times 10^5$ | – | – | – | 31 | 306 |
| 3 | $8.1 \times 10^5$ | – | – | – | 31 | 307 |
| 4 | $8.1 \times 10^5$ | – | – | – | 31 | 307 |
| 5 | $8.1 \times 10^5$ | – | – | – | 29 | 306 |
| 6 | $8.1 \times 10^5$ | – | – | – | 30 | 305 |
| 7 | $8.1 \times 10^5$ | – | – | – | 29 | 308 |

TABLE II-continued

| Test | Initial CFU | Septum CFU | Specimen CFU | Media CFU | Time to Max. Temperature(s) | Max. T (° C.) |
|---|---|---|---|---|---|---|
| 8  | $8.1 \times 10^5$ | – | – | – | 31 | 308 |
| 9  | $8.1 \times 10^5$ | – | – | – | 29 | 308 |
| 10 | $8.1 \times 10^5$ | – | – | – | 28 | 308 |
| 11 | $1.6 \times 10^6$ | – | – | – | 33 | 305 |
| 12 | $1.6 \times 10^6$ | – | – | – | 31 | 304 |
| 13 | $1.6 \times 10^6$ | – | – | – | 31 | 305 |
| 14 | $1.6 \times 10^6$ | – | – | – | 30 | 306 |
| 15 | $1.6 \times 10^6$ | – | – | – | 32 | 305 |
| 16 | $1.6 \times 10^6$ | – | – | – | 33 | 306 |
| 17 | $1.6 \times 10^6$ | – | – | – | 33 | 306 |
| 18 | $1.6 \times 10^6$ | – | – | – | 32 | 308 |
| 19 | $1.6 \times 10^6$ | – | – | – | 34 | 309 |
| 20 | $1.6 \times 10^6$ | – | – | – | 29 | 306 |
| 21 | $1.6 \times 10^6$ | – | – | – | 31 | 305 |
| 22 | $1.6 \times 10^6$ | – | – | – | 32 | 305 |
| 23 | $1.4 \times 10^6$ | – | – | – | 29 | 307 |
| 24 | $1.4 \times 10^6$ | – | – | – | 30 | 305 |
| Specimen Introduction Test - 305° C., 500 µL H$_2$O. | | | | | | |
| 25 | $1.4 \times 10^6$ | – | – | – | 30 | 307 |
| 26 | $1.4 \times 10^6$ | – | – | – | 30 | 306 |
| 27 | $1.4 \times 10^6$ | – | – | – | 31 | 305 |
| 28 | $1.4 \times 10^6$ | – | – | – | 30 | 307 |
| 29 | $1.4 \times 10^6$ | – | – | – | 30 | 306 |
| 30 | $1.4 \times 10^6$ | – | – | – | 30 | 305 |
| 31 | $1.4 \times 10^6$ | – | – | – | 29 | 305 |
| 32 | $1.4 \times 10^6$ | – | – | – | 31 | 306 |

+ = Survivors Present
– = No Survivors Present

What is claimed is:

1. A method for sterile transfer of a fluid sample to or from a biological system, comprising:
   connecting a specimen transfer device having a penetrable septum to a sterilization chamber including a penetrating element for fluid communication with the biological system;
   placing a quantity of water in the sterilization chamber;
   irradiating the sterilization chamber with microwave energy to vaporize the water and superheat the resulting steam to sterilize the sterilization chamber and an exposed surface of the septum;
   penetrating the septum with the penetrating element to establish fluid communication between the specimen transfer device and the biological system.

2. The method of claim 1 wherein the specimen transfer device comprises a septum holder connected to the septum, a transfer tube sealed to the septum holder, and a syringe attached to the transfer tube.

3. The method of claim 2 further comprising operating a barrel in the syringe to transfer the sample between the syringe and the biological system.

4. The method of claim 1 wherein the biological system comprises a flow-through valve and wherein the method further comprises moving the valve between a sterilization position wherein the sterilization chamber is sealed and an access position wherein the penetrating element is in fluid communication with the flow-through valve.

5. The method of claim 1 wherein the penetrating element comprises a needle stub tube.

6. The method of claim 1 wherein the sterilization chamber comprises a wall made of a material having a strong dielectric loss characteristic.

7. The method of claim 1 wherein a maximum duration of the irradiation is controlled by either a temperature switch connected to a thermocouple adjacent to the sterilization chamber or a maximum fixed time set by a time delay relay.

8. The method of claim 1 further comprising the step of sealing the sterilization chamber prior to the irradiation.

9. The method of claim 8 wherein a position of the specimen transfer device relative to the sterilization chamber is controlled by a three-position cam having an open position in which the septum is spaced from the sterilization chamber to allow the quantity of water to be placed in an open port of the sterilization chamber, a sterilization position in which the septum is received in the port to seal the sterilization chamber, and an access position in which the septum is pierced by the penetrating element.

10. The method of claim 1 further comprising opening a vent from the sterilization chamber after the irradiation and before the septum penetration.

11. Apparatus for sterile transfer of a fluid sample to or from a biological system, comprising:
    a sterilization chamber having an inlet port;
    a specimen transfer device having a septum-sealed end adapted to be received in and seal the inlet port;
    a needle stub tube in fluid communication between the sterilization chamber and a flow-through valve to the biological system, the valve having a closed position preventing fluid communication between the needle stub tube and the biological system and an open position to allow fluid communication between the needle stub and the biological system;
    a microwave power supply for irradiating the sterilization chamber with microwaves;
    wherein the specimen transfer device is movable with respect to the needle stub tube to pierce the septum with the needle stub tube.

12. The apparatus of claim 11 wherein the sterilization chamber has a wall made of a material having a strong dielectric loss characteristic.

13. The apparatus of claim 12 wherein the wall is made of silicon carbide.

14. The apparatus of claim 11 wherein the specimen transfer device comprises a septum holder connected to the septum, a transfer tube connected to the septum holder and a syringe connected to the transfer tube.

15. The apparatus of claim 11 comprising a rotating cam for positioning the specimen transfer device relative to the sterilization chamber between an open position wherein the septum is spaced from the inlet port, a sterilization position wherein the septum is received in the inlet port to seal the sterilization chamber but spaced from the needle stub tube, and an access position wherein the needle stub tube penetrates the septum.

16. The apparatus of claim 11 further comprising a pressure release valve for venting the sterilization chamber.

17. The apparatus of claim 11 further comprising a control circuit for operating the microwave power supply including a temperature switch connected to a thermocouple adjacent to the sterilization chamber to turn off the microwave power supply when the sterilization chamber reaches a predetermined temperature, and a time delay relay to turn off the microwave power supply if the microwave power is supplied for a predetermined period of time.

18. The apparatus of claim 11 further comprising a coaxial cable connected between the microwave power supply and the sterilization chamber.

19. The apparatus of claim 18 wherein the microwave power supply comprises a magnetron, a transmission antenna disposed between a fixed end-plate and a variable end-plate, and a pick-up antenna from the coaxial cable disposed between the end-plates, wherein the variable end-plate is adjustable to tune the microwave power supply.

* * * * *